United States Patent
Bleustein et al.

(10) Patent No.: US 7,097,622 B2
(45) Date of Patent: Aug. 29, 2006

(54) NON-INVASIVE, QUANTITATIVE SOMATOSENSORY APPARATUS FOR THE EVALUATION OF ERECTILE DYSFUNCTION

(76) Inventors: Clifford B. Bleustein, 40 E. 78th St., New York, NY (US) 10021; Joseph Arezzo, 34 Hampshire Rd., Mahwah, NJ (US) 07430; Arnold Melman, 23 Agnes Cir., Ardsley, NY (US) 10502

( * ) Notice: Subject to any disclaimer, the term of this patent is extended or adjusted under 35 U.S.C. 154(b) by 0 days.

(21) Appl. No.: 10/851,861

(22) Filed: May 21, 2004

(65) Prior Publication Data
US 2005/0010129 A1    Jan. 13, 2005

Related U.S. Application Data

(63) Continuation-in-part of application No. 10/252,288, filed on Sep. 23, 2002, now abandoned.

(60) Provisional application No. 60/388,002, filed on Jun. 12, 2002.

(51) Int. Cl.
*A61B 5/00* (2006.01)
*A61B 19/00* (2006.01)
(52) U.S. Cl. .................. 600/555; 600/557; 128/898
(58) Field of Classification Search ............... 600/300, 600/549, 552, 553, 555–557, 38, 587; 128/897, 128/898; 606/20–30; 607/96–99, 108
See application file for complete search history.

(56) References Cited

U.S. PATENT DOCUMENTS 4,763,666 A * 8/1988 Strian et al. ............... 600/554
5,191,896 A * 3/1993 Gafni et al. ............... 600/555
6,679,908 B1 * 1/2004 Shimizu .................... 607/109
6,741,895 B1 * 5/2004 Gafni et al. ............... 607/138

OTHER PUBLICATIONS

Physitemp: Quantitative Sensory Testing Equipment, http://web.archive.org/web/19991004165517/http://www.physitemp.com/sensory.htm, Oct. 4, 1999.*
Yarnitsky et al, Penile Thermal Sensation, The Journal of Urology, vol. 156(2), Aug. 1996, pp. 391-393.*
Lefaucheur et al, Relationship Between Penile Thermal Sensory Threshold Measurement and Electrophysiologic Tests to Assess Neurogenic Impotence, Adult Urology, 2001.*
Lefaucheur et al, Assessment of Penile Small Nerve Fiber Damage After Transurethral Resection of the Prostate by Measurement of Penile Thermal Sensation, The Journal of Urology, vol. 164, Oct. 2000.*

* cited by examiner

*Primary Examiner*—Charles Marmor
(74) *Attorney, Agent, or Firm*—Keith D. Nowak; Carter Ledyard & Milburn, LLP

(57) ABSTRACT

A non-invasive quantitative somatosensory apparatus is provided for evaluating erectile dysfunctions and involves the applications to the glans penis of two different temperatures. If the patient is unable to differentiate the difference in temperature, a diagnosis of neurologic dysfunction can be made with greater than 90% reliability. The apparatus of this invention provides a relatively simple device to assess a patient's neurological response to therapies.

21 Claims, 1 Drawing Sheet

NON-INVASIVE, QUANTITATIVE SOMATOSENSORY APPARATUS FOR THE EVALUATION OF ERECTILE DYSFUNCTION

RELATED APPLICATIONS

This application is a Continuation-in-Part of U.S. application Ser. No. 10/252,288, filed Sep. 23, 2002, now abandoned and incorporated herein by reference, which claims benefit of U.S. Provisional Application Ser. No. 60/388,002, filed on Jun. 12, 2002.

FIELD OF THE INVENTION

This invention relates to a simple non-invasive apparatus for the evaluation of erectile dysfunction (ED). The results obtained can be useful to assess a patient's neurological response to therapies.

BACKGROUND OF THE INVENTION

Erectile dysfunction (ED) is defined as the inability to achieve or maintain an erection sufficient for satisfactory sexual performance. The prevalence in United States is 10 to 20 million men. The male erectile response is a neurovascular event reliant on the complex interaction between neurological and vascular responses. Erectile dysfunction is multifactoral and has been typically classified by the primary presumed cause: vasculogenic, psychogenic, neurogenic, and endocrinologic disease. Any condition or injury that impairs the transmission of impulses along the psychogenic or reflexogenic neurological pathway, may be associated with neurogenic erectile dysfunction.

The penis is innervated by the dorsal penile and perineal nerves. These nerves are a continuation of sympathetic and parasympathetic autonomic nerves as well as sensory and motor somatic nerves. The somatic sensory system is responsible for the specialized structures that transmit information about the external environment. There are four major classes of somatic sensation: pain, temperature, position sense, and touch-pressure sensation. These stimuli are transmitted in the autonomic nervous system through both large ($ and b) and small (b and C) caliber nerves.

Currently, as many tests are available to evaluate the sensory afferent nerves from the penile skin, as well as the motor efferent nerves to the perineum. These tests include the bulbocavernosus reflex, penile thermal sensory threshold measurement, corpus cavernosum electromyogram (CC-EMG) signal assessment, somatosensory evoked potentials, anal or urethral sphincter EMG, and vibration perception sensitivity. The problems with many of these tests is that they tend to be complex, time consuming, and do not directly measure autonomic function or correlate with the degree of ED.

The study leading to the present invention was designed to test the hypothesis that autonomic neuropathy is a significant component of ED, and further, that this deficit could be evaluated by measuring specific aspects of sensation in the nerves innervating the penis. This study was also designed to evaluate the impact of age and concomitant medical conditions, such as diabetes on the loss of cutaneous sensation of the penis.

In recent years, quantitative sensory testing (QST) has emerged as an important adjunct of the neurologic examination and its use has been recommended by several consensus panels including: American Neurologic Association, American Diabetes Association and the Peripheral Nerve Society. A variety of QST instruments and testing algorithms have been developed and utilized to provide standardized, non-invasive and semi-objective measures of neural function. These procedures have proven valuable in tracing the onset and progression of peripheral neuropathy associated with aging, disease, exposure to exogenous neurotoxins and in documenting iatrogenic neuropathies associated with the treatment of cancer and HIV infection. Validated equipment and procedures exist for the testing of vibration, pressure, spatial perception, warm, cold and painful stimuli. The approach is to provide well controlled, standardized sensory stimuli and to evaluate detection threshold using established psychophysical procedures, such as ascending method of limits, and two alternative forced choice. For instance, a simple hand-held device, the Semmes-Weinstein monofilament has been found a valuable method of screening for deficits in pressure sensation, while the Tactile Circumferential Discriminator has been used to screen for neuropathy and foot ulcer risk.

While most tests of QST have focused on sensation in the hands and/or feet, a few studies have used this approach to evaluate sensation in the genital region. Romanzi et al. found that Semmes-Weinstein monofilaments could be used to evaluate pressure/touch sensitivity of the female external genitalia and various devices have been used to measure vibration thresholds at the penis. A recent review of 13 studies on vibrotactile penile thresholds of men with ED were significantly higher (diminished sensitivity) than age-controlled functional males. Yarnitsky et al. found that penile thermal thresholds could be used as a repeatable, valid diagnostic tool to evaluate somatic small fiber function and reported normative values. Lefaucheur expanded the use of penile thermal thresholds, and demonstrated higher thresholds in impotent diabetic males.

SUMMARY OF THE INVENTION

The present invention therefore provides a simple, non-invasive quantitative somatosensory apparatus for evaluating erectile dysfunctions.

Accordingly, one or more of the following objects can be achieved by the present invention. It is an object of the invention to provide an apparatus for the evaluations of erectile dysfunctions. Another object of the invention is to provide a simply non-invasive method. A further object is to provide a method which can be conducted in a relatively short time.

These and other objects will be readily apparent to those skilled in the art in the light of the teachings herein set forth.

In its broad aspect the present invention relates to, an apparatus for the evaluation of erectile dysfunction. The apparatus is a non-invasive, quantitative, somatosensory device which comprises means for applying heat incrementally to the glans penis of a male patient starting at acclimation temperature until the patient can correctly identify which temperatures was warmer for at least two consecutive times. Such temperature is noted on the thermal threshold for warmth and correlates closely with the erectile functions domain of the International Index of Erectile Function (IIEF). The apparatus is designed to be adjustable between about 32° and 36° C. without a cooling reservoir.

DESCRIPTION OF THE PREFERRED EMBODIMENTS

Figure 1:
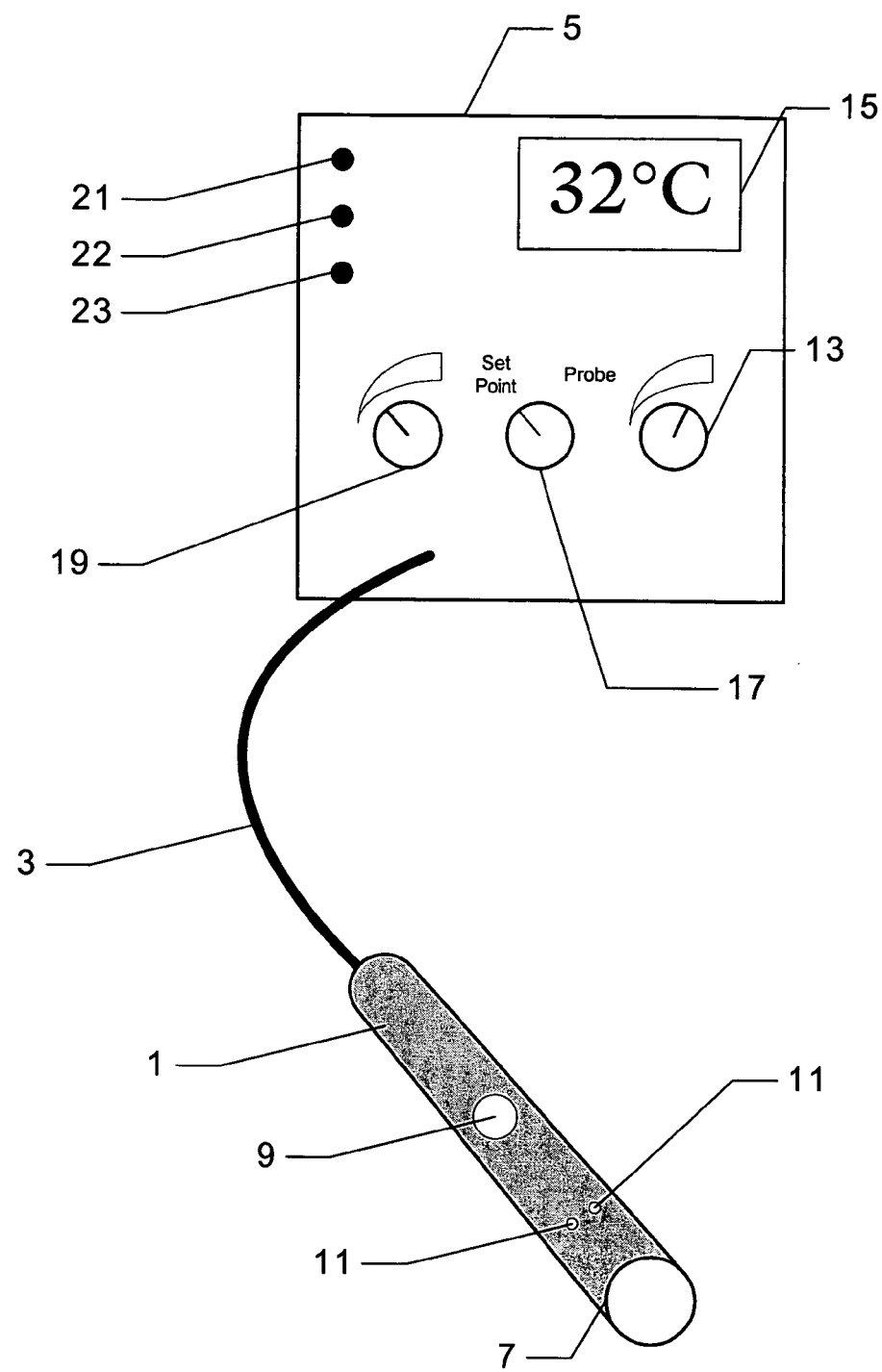
FIG. 1 is a depiction of one embodiment of the apparatus.

In practice, it has been found that optimum results are obtained if the initial temperature at which the test method is commenced is acclimation temperature, and more preferably about 32° C. The temperature is raised in increments of about 1° C. over a period of time sufficient for the patient to detect that there is a change in temperature from the previous temperature. This can be anywhere from a few seconds to several seconds or longer depending upon the patient.

As noted hereinafter, the instrument employed to conduct the test method is a thermal sensitivity tester wherein incremental changes of preferably 1° C. or less can be accurately controlled and measured.

In one embodiment of the invention, as shown in FIG. 1, the instrument includes a hand-held thermode probe 1 about ½" in diameter and 6" long, including its handle, with a 5' lead 3 connecting a separate control unit 5. Preferably, the lead 3 is adapted to removeably connect, at its ends, to either or both probe 1 and controller 5. Preferably, four 1.5 volt alkaline batteries power the system. Alternatively, the device is powered using an A/C source and a D/C adaptor.

The tip of the probe 7 is capable of being driven at least two switch-selectable temperatures, using proven Peltier thermoelectric technology. Two of the selectable temperatures are preferably 32° and 36° Centigrade. A switch 9 on the probe will turn on the unit and allow selection of either of the two temperatures. Alternately, a dial or other adjustment means is used to select a start temperature. In one embodiment, LED lamps 11 mounted in the handle will indicate when the unit is turned on and will begin flashing when the switch is depressed and temperature is changing. The lamp will come on continuously to indicate when the temperature of the thermode has reached set point (preferably, within 8 seconds). A timer in the control unit will automatically turn off power if the temperature is not changed within five minutes, to preserve battery power.

Accuracy of the set points is preferably + or −0.3° Centigrade. The test protocol is non-invasive and the 6 volt battery power (or other power source) provides for patient safety. There is also an over-temperature shut-off circuit which turns off the unit if heat sink temperature exceeds 40° C. A detector circuit monitors the status of the thermal probe. The various states of the thermal probe include connected and disconnected conditions. In one embodiment, the detector circuit and the overheating circuit are combined.

The Controller is a testing instrument, which provides a means of accurately measuring a subject's ability to distinguish small differences in temperature. The thermal probe is driven by a thermoelectric (Peltier effect) module. This module has the ability to provide temperature stimuli above and below room temperature.

The temperature of the probe tip is adjusted using a set switch 13, which is used to maintain the temperature at the set point. The set switch can be located on the probe or the controller. A digital readout (display) 15 on the controller displays the temperature set point. In one embodiment, a switch 17 toggles the display from the set point to the probe temperature.

In previous devices, for stable operation, the thermoelectric module required a trickle of cooling water. This was typically supplied from a pump and tank unit. However, based on the temperature ranges used, and accurate control circuitry, no cooling reservoir is required. Without a cooling reservoir, there is no risk of the reservoir leaking thereby damaging the unit.

Preferably, adjustment may be made to any base temperature between 20° and 40° Centigrade to within 0.1° C. Temperature settings 19 can be made using the control settings on the controller or probe. These settings allow the temperature to be incremented or decremented in 5° 1° or 1/10° steps from the base temperature.

The digital readout (display) 15 of the controller may be used as a readout for an external sensor (Type T, copper-constantan thermocouple with miniature t/c plug) used to verify the temperature of probe tip 7.

During measurement with external sensor, all power to the Probe is preferably disconnected.

In one embodiment, the controller 5 includes a low power indicator 21. The indicator is an LED that illuminates when a lower power condition exists or it can be a meter that displays an actual power level. In one embodiment, controller 5 includes an overheating circuit. The overheating circuit shuts down the unit if the temperature exceeds a set point. In one embodiment, when an overtemperature condition exists, an indicator 22 illuminates.

The controller 5 preferably includes a sensor detector circuit and a sensor detector indicator 23. The sensor detector detects if the probe 1 is properly connected and functioning. If no probe is connected to controller 5, or if the probe is not functioning properly, the indicator 23 will display an alarm. In one embodiment of the invention, the alarms are audible as well as visible.

As also noted in the Examples, a thermal threshold can also be determined by incrementally lowering the temperature at 1° C. intervals from 32° C. until such time as the patient can detect a difference from the previous temperature for at least two and preferably up to 6 times.

The results of the study leading to the present inventions greatly expand the use of QST in the evaluation of neural function at the penis and provide unique information about the correlation of sensory function and ED. To applicant's knowledge, the present study is the first to apply this technique for the evaluation of the neurophysiology of the penis. Specifically these results confirm that patients with ED, regardless of etiology, have broad-based (not unique to one neural fiber group) deficits detected with multiple modalities and testing procedures when compared with normal controls. Applicants are the first to utilize pressure (Semmes-Weinstein monofilaments) and spacial perception (the Tactile Circumferential Discriminator) for assessing neuropathy of the penis and demonstrated increased thresholds (worse functioning) for patients with complaints of ED. Applicants further confirmed large fiber axonal dysfunction with increased vibration (Biothesiometer) thresholds in patients with ED. Also the first to assess small fiber axonal function with warm and cold thresholds in non-diabetic patients with ED and demonstrated worse functioning when compared to normal controls.

The results obtained suggest that neuropathy at the penis exists in all forms of erectile dysfunction including arterial and venous disease. Additionally, in some cases (e.g. diabetes) dysfunction of the penile nerves antecedes deficits in cutaneous function detected at the finger (general neuropathy). This leads one to believe that in cases such as diabetes, there may be a different underlying cause for the erectile dysfunction than the classically taught chronically progressive, length-dependent, distal axonopathy of the dying-back type. Since neurologic erectile dysfunction may be related to multiple causes including chronic diseases (e.g. diabetes mellitus, multiple sclerosis, Parkinson's disease, Alzheimer's disease), surgery or trauma (e.g. radical retro-pubic prostatectomy, herniated lumbar disk), and neural malformation (spina bifida) to name a few, multiple factors may be responsible for the neurological defects that were seen in studies. Loss of sensation may be related to a change in fiber density (loss of axons-distal axonopathy), deficits in transduction (generator potential), deficits in conduction (velocity synchrony), or non-structural defects such as redistribution of ion channels. The exact mechanism of neuropathy remains to be elicited in future research.

In order to determine which patients had erectile dysfunction, all participants were required to complete the erectile function domain of the IIEF. This test has been widely used by the pharmaceutical industry to assess the outcomes of drug therapy through non-invasive, self-assessment questionnaires. The erectile function domain of the IIEF has been validated in multiple studies as a reliable test, not only for determining which patients have ED, but also for assessing the severity of function. Despite its widespread use in clinical trials assessing function before and after medical intervention, it is believed that only one group has tried to compare the IIEF to current erectile dysfunction testing. Blander et al. demonstrated that the IIEF score did not differentiate between the specific etiologies of ED as determined by penile blood flow studies and testing with prostaglandin E.sub. 1 testing had now IIEF scores of 13/25. In contrast to their study, applicants found a significant correlation between the IIEF score (encompassing patients with all forms of erectile dysfunction) and neurophysiological measurements of touch, pressure, vibration, and thermal discrimination. This suggests that the IIEF may be a good questionnaire to assess the neurological component of erectile dysfunction.

While the study leading to the present invention provides several insights into the neuropathy of ED, it is limited by both the sample and the methods of QST. Applicants chose to use a sample of patients from the academic urology offices. These patients may not be representative of the normal population or the population of individuals seen in a typical medical or primary care clinic. In order to improve the understanding of normal penile aging and function, as well as provide accurate confidence intervals for cut scores defining ED, a larger normal population from the general population should be obtained. While QST is non-invasive, easy to perform in an office setting, reproducible, and well suited for multicenter trials, QST does have some limitations. QST is a psychophysical test and requires the cooperation, attention, and motivation of the patient. QST has been typically used for the detection of peripheral receptors which must be processed centrally and therefore requires integrity of the entire neural pathway (i.e. pathology anywhere along the way may affect results). While QST has limitations, the present results remained consistent with the literature. A significant correlation between age and Semmes-Weinstein monofilament testing and tactile circumferential discriminator of the finger has been demonstrated which are consistent with cutaneous pressure threshold and two-point discrimination studies which demonstrate a deterioration with aging. The vibrotactile penile thresholds were also in agreement with a recent review of 13 studies which found that threshold levels increased as a function of age and that penile thresholds of men with ED were significantly higher than age-controlled functional males. The measurements of cold threshold of the finger is in agreement with a study by Gelber et al. who looked at cooled temperature thresholds of the dominant finger and found no association between thermal perception thresholds and age. Finally, in agreement with Lefaucheur et al., we found that there was a significant difference with both warm and cold thresholds when comparing those with ED and normal controls at the penis.

The present inventors evaluated the functional integrity of the penile autonomic nervous system in patients with erectile dysfunction. We demonstrated dysfunction of the large (♦ and ♭) caliber fibers with significant differences between normal controls and ED patients with pressure, spatial perception, and vibration. We also demonstrated impairment in the small (♦ and C) caliber nerves with significantly increased cold and warm thresholds in ED patients. We also found that as people age, there is a significant loss of pressure and vibration sensitivity of both the glans penis and the finger. It also appears that the loss of vibration sensitivity is particularly significant for the diabetic patient. Whether all of these changes are the end result of ED or the cause of erectile dysfunction remains to be elicited, but neuropathy appears to be a significant aspect of all forms of erectile dysfunction. These techniques give us a new way of assessing a patient's neurological response to therapies. They could be used in a longitudinal fashion to study changes over time in an office setting.

The following examples are illustrated:

Patients and Materials: Seventy-three patients who visited the academic urology clinics at Montifiore hospital in New York city were evaluated. All patients were required to complete the erectile function domain of the International Index of Erectile Function (IIEF) questionnaire; 20 subjects had no complaints of ED and scored within the "normal" range on the IIEF. Patients were subsequently tested on their index finger and glans penis for vibration (Biothesiometer), pressure (Semmes-Weinstein monofilaments), spatial perception (Tactile Circumferential Discriminator), and warm and cold thermal thresholds.

Impaired blood flow to the penis is the most common cause of ED. While altered neural function is generally regarded as a second critical component of ED, this factor is difficult to assess and its contribution may therefore be underestimated. Both the dorsal penile and perineal nerves contain a variety of axons that differ in cross sectional diameter and the presence and degree of myelin. A careful consideration of the impact of neural deficits on erectile function must differentiate between activities conducted in small diameter fiber pathways (i.e. ♦and unmyelinated C fibers) and activity conveyed in relatively large diameter, myelinated fiber systems (♦ and ♭). The assessment of sensory function provides a non-invasive means of assessing the integrity of the neural inervation of the penis, and the evaluation of multiple modalities affords the ability to differentiate function within specific axon types. For instance, the determination of absolute threshold for the detection of vibration, spatial perception and pressure measures transduction and conduction of large fiber function while thermal thresholds provides an index of activity in unmyelinated C fiber pathways (warm) and small myelinated A♭ fibers (cold).

Methods:

All procedures were approved by the Institutional Review Board for the protection of human subjects in research at Montefiore Medical Center. As noted above, a total of 73 patients from the department of Urology participated in the study. These patients were accrued from Dec. 1, 2001 to Feb. 28, 2002. It is believed that these subjects are a representative sample of the patients visiting the academic urology clinics, however no formal sampling strategy was utilized. Normal controls were sent for urological evaluation of problems not relating to erectile dysfunction, while other physicians typically referred patients with complaints of erectile dysfunction for evaluation at the clinic. The patients were comprised of 37% Caucasian (27/73), 25% African American (18/73), 23% Hispanic (17/73), and 15% (11/73) of the patient population was unidentified. The demographics of the patients are presented in Table 1. Any person unable to understand English was excluded from participation. After consent was obtained, a medical history was recorded from each subject with a focus on any history of diabetes or hypertension. Patients were asked to complete the erectile function domain of the International Index of Erectile Function (IIEF) questionnaire. The IIEF is scored on a 1–30 scale; a score of 25 or greater represents no dysfunction, while a score less than 25 identifies those patients with erectile dysfunction. In the cohort evaluated, 20 subjects (27.4%) scored within the normal range and constituted no ED group, while 53 subjects (73.6%) had evidence of ED by history (ED Group). The battery of sensory evaluation was obtained in all subjects, with tests performed by the same researcher (CB). All sensory evaluations were performed on the palmar aspect of the distal right index finger. Additional measurements were recorded on the dorsal midline glans of the penis halfway between the coronal sulcus and the urethral meatus. In males who were not circumcised, the foreskin was retracted and the measurements were taken on the dorsal midline glans.

All thresholds were obtained using a modified ascending method of limits or a two alternative forced choice procedure. Vibration was determined using a biothesiometer device (Bio-Medical Instrument Co., Newbury, Ohio). Stimulus frequency was a fixed 120 Hz signal; intensity was roughly proportionate to the square of the applied voltage be measured by a sensitive galvanometer. As the voltage was gradually elevated, the subject identified the minimal energy at which he could distinguish between vibration and static touch. Thresholds were recorded both from the palmer aspect of the distal right index finger and from the glans of the penis. All measurements were first performed on the finger, followed by the dorsal midline of the glans.

Sensitivity to touch was determined by use of the Semmes-Weinstein monofilament technique (North Coast Medical, Inc., Morgan Hill, Calif.). Briefly, subjects were contacted at the test site by a series of monofilaments of ascending intensity and threshold was defined as the smallest stimulus intensity correctly identified as a definite sensation of light pressure. Filaments were applied perpendicular to the skin for a period of approximately 1.5 seconds. The diameter of the filament (in millimeters), and therefore the intensity of the stimulation, increased from 2.83, 3.61, 4.31, 4.56, 5.07, to 6.65 which corresponds to an increase in target force of 0.07 grams, 0.4 grams, 2.0 grams, 4.0 grams, 10 grams, and 300 grams respectively. The target forces of 0.07 grams and 0.4 grams were repeated for a total of 3 trials before the higher intensities were examined successively. Thresholds were first determined on the palmar aspect of the right index finger and afterward the glans.

Spatial threshold was determined using the tactile circumferential discriminator (Wyeth-Ayerst International Inc., Westtown, Pa.). This device consists of a series of eight aluminum rods that vary in cross sectional diameter and therefore in circumference from 12.5 mm to 40 mm. The subject is initially presented with a reference rod (labeled 0) placed firmly against the skin for a period of approximately 2 seconds and then with a "test" rod (numbered 1–7) that differs in circumference. Threshold is determined as the smallest difference in circumference that can be reliably detected on six consecutive trials. This procedure evaluates the spatial properties of sensation (i.e. minimal separation, number and distribution of activated receptors) and is similar to the measurement of two-point discrimination thresholds. Thresholds were again determined first on the index finger and then on the glans of the penis. A subject unable to differentiate between 7 and 0 was assigned the highest threshold (i.e. score of 8).

Hot and cold thermal thresholds were determined using a two alternative forced choice procedure on both the penis and index finger. At each site the subject was presented with a thermal signal generated by a device, as discussed herein. Stimuli were presented against the skin using a hand-held thermal probe, capable of delivering both hot and cold temperatures over a 40° temperature range. The probe was set to an acclimation temperature of 32° C. and all comparisons were made against this reference. The temperature was increased at increments of 1° C. until the patient was able to correctly identify which temperature was warmer six times consecutively. That temperature was then recorded as the thermal threshold for warmth. The same procedure was followed for cold discrimination with the temperature decreased at increments of 1° C. In order to control for the possibility that any differences observed were due to differences in cutaneous temperatures between no ED and ED, surface skin temperature was measured at the test site in a subset of subjects. The assessment of thermal thresholds was labor intensive and time consuming. Not all subjects elected to participate in this assessment. Thermal thresholds were determined in a total of 36 subjects (28 with ED and 8 without ED).

The following parameters were evaluated: age, history of diabetes, history of hypertension, measurement of tactile circumferential discrimination of the glans and finger, biothesiometry of the glans and finger, warm temperature threshold of the finger and glans, cold temperature threshold of the finger and glans. Analysis for the tactile circumferential discriminator was performed both with the stated number and with the converted diameter in inches. Analysis for the SWM was also performed for both the labeled diameter of the filament and the corresponding value of force in grams. Univariate distributions were assessed for normality. Bivariate relationships were assessed using chi square, t test, and Pearson correlations. Composite null hypotheses were assessed with mixed models repeated measures analysis of variance using SAS PROC MIXED (V.8.1, 2001), allowing us to covary for age, diabetes, and hypertension.

Results

The demographics of the 73 patients are presented in table 1 below. The mean age was 48.8 (range 21–77) and 55.0 (range 22–81) for no ED and ED, respectively. Although the subjects with ED were slightly older, the age difference between groups was not significant ($r$-0.12). As expected, the IIEF score tended to be reduced (greater evidence of ED) as a function of age (r-0 14), however the correlation was again not significant (p=0.24)

TABLE 1

Demographics of 73 patients.

|  | No ED | ED |
|---|---|---|
| N | 20 | 53 |
| IIEF (mean) | 28.4 | 13.4 |
| AGE .±-. STD | 48.8 .±-. 15.0 | 55 .±-. 14.9 |
| HTN | 7 (35%) | 20 (38%) |
| DM | 2 (10%) | 15 (28%) |

TABLE 2

Mean .+-. SEM neurophysiological testing values for the glans penis.

|  | Tactile Circumferential Discriminator* | Semmes-Weinstein Monofilaments | Biothesiometer* | Cold threshold* | Warm threshold* |
|---|---|---|---|---|---|
| No ED | 4.80 .±-. 0.42 | 0.90 .±-. 0.24 | 3.95 .±-. 0.40 | 29 1 .±-. 0.55 | 35.8 .±-. 0.45 |
| ED | 6.52 .±-. 0.23 | 3.54 .±-. 0.44 | 7.72 .±-. 0.80 | 24.4 .±-. 0.38 | 39 6 .±-. 0.35 |

+p = 0.001
*p = <0.0001

TCD values are the labeled number. The monofilament values are the diameter of the monofilaments converted into the corresponding target force in grams The *er* values remained significant for the monofilaments when analysis was performed for reported monofilament diameter. The biothesiometer measurement is the relative value stated on the biothesiometer. The warm and cold thresholds are reported in ° C.

TABLE 3

Pearson Correlation Coefficients of the glans penis and IIEF score

|  | TCD* | SWM* | Biothesiometer* | Cold threshold* | Warm threshold* |
|---|---|---|---|---|---|
| Glans r value | −0.48 | −0.38 | −0.35 | 0.60 | −0.58 |

TABLE 4

Mean .+-. SEM neurophysiological testing values for the finger

|  | Tactile Circumferential Discriminator* | Semmes-Weinstein Monofilaments | Biothesiometer* | Cold threshold* | Warm threshold* |
|---|---|---|---|---|---|
| No ED | 2.55 .±-. 0.30 | 0.29 .±-. 0.02 | 3.51 .±-. 0.30 | 30.1 .±-. 0.52 | 34.0 .±-. 0.33 |
| ED | 2.65 .±-. 0.23 | 0.27 .±-. 0.04 | 4.02 .±-. 0.30 | 29.4 .±-. 0.30 | 35.0 .±-. 0.45 |

TCD values are the labeled number. The monofilament values are the diameter of the monofilaments converted into the corresponding target force in grams. The *er* values remained not significant for the monofilaments when analysis was performed for reported monofilament diameter. The biothesiometer measurement is the relative value stated on the biothesiometer. The warm and cold thresholds are reported in ° C.

When measured at the glans of the penis, threshold values for each of the five sensory modalities evaluated were significantly increased (diminished sensation) in those with ED as compared to values of those with no ED (Table 2). For instance, the threshold for the detection of a stimulus as "cold" was approximately 4.7° C. lower (further from reference temperature) for ED group as compared to no ED ($p<0.0001$). Similarly, while a stimulus was perceived as "warm" when it was an average of 3.8° C. above the reference temperature in subjects without ED, it needed to be more than 7.6° C. above reference to be detected as "warm" in the subjects with ED, Modalities associated with both small diameter axons (i.e. temperature) and large diameter axons (i.e. pressure, vibration, spatial threshold) were all sharply different across groups. The differences in mean values at the penis across groups remained significant for each of the neurophysiologic measures (except vibration, $p<0.06$) even after controlling for age, diabetes and hypertension.

The deficit in sensory function was consistently greater in patients with worse ED, resulting in highly significant correlation between each of the five neurophysiological measurements of the penis and the patient's IIEF score (Table 3). Each of the correlations was in the expected direction (Table 3). The correlation of each measure and IIEF scores also remained significant after controlling for age, diabetes and hypertension ($p<0.05$).

Since resident skin temperature may have an effect on cutaneous sensation, especially thermal thresholds, we examined the surface temperature of the skin overlying the glands in a limited random sample of subjects in no ED and ED groups The mean temperature of subjects in subjects without ED was 31.8° C. (N=2), and is not distinguishable from the mean cutaneous temperature of the glans in patients with erectile dysfunction (31.9° C., n=11).

In contrast to the results obtained at the penis, there were no significant differences between no ED and ED groups in cutaneous sensory thresholds measured at the finger (Table 4) Only one measure, warm threshold, strongly trended in the direction of decreased function in subjects with ED (*er*=0.07). In addition, there was no significant correlation between any of the five thresholds examined at the finger and patient's IIEF scores.

Diabetes and hypertension, as well as age, may also influence sensation. The prevalence of hypertension was similar across groups. Of those patients with a history of hypertension 74.1% also reported erectile dysfunction compared with 71.7% of the population without ED. Regression models using age, hypertension, and diabetes as covariates demonstrated that hypertension, for all neurophysiologic measurements of both the penis and finger, was not significant, indicating that hypertension does not contribute to the results obtained. Of those patients with a history of diabetes, 88.2% also reported erectile dysfunction as compared with 67.9% of the population who reported no history of diabetes. There was a significant contribution (based on regression analysis) associated with diabetes and measurements of vibration at the penis (p=0.003). We also demonstrated a significant contribution by diabetes to warm threshold (p=0.04) at the penis and to tactile circumferential discriminator at the finger (p=0.04). Although diabetes contributed significantly to vibration and warm threshold at the penis, its impact on these measurements did not outweigh the overall differences between those with ED and normal controls. Age is a third subject variable that might alter sensory thresholds. As expected, in the present study there was a significant correlation between increasing age and worsening cutaneous sensation of the finger to vibration, pressure and spatial resolution (based on regression analysis (p<0.05). Again, the contribution of age towards the cutaneous measurements did not obscure the overall differences between those patients with ED and normal controls.

Sensation on the glans penis, as defined by the examined sensory thresholds, was significantly diminished in patients with ED and these differences remained significant when controlling for age, diabetes, and hypertension. In contrast, thresholds on the index finger were equivalent in the ED and non-ED groups. Threshold and IIEF scores were highly correlated, consistent with an association between diminished sensation and decreasing IIEF score (worse erectile functioning). These relations also remained significant when controlling for age, diabetes, and hypertension.

The findings demonstrate dysfunction of large and small diameter nerve fibers in patients with ED of all etiologies. Further, the neurophysiologic measures validate the use of the IIEF as an index of ED, as objective findings of sensory neuropathy were highly correlated with worse IIEF scores. The sensory threshold methods utilized represent novel, non-invasive and relatively simple procedures, which can be used in a longitudinal fashion to assess a patient's neurological response to therapies.

The method of this invention can also be supplemented, if desired, by determination of the spatial perception threshold and/or the application of pressure, i.e., the sensitivity to touch determination to provide a two-point determination.

Although the invention has been illustrated by the preceding examples, it is not to be construed as being limited to the materials employed therein, but rather, the invention relates to the generic area as hereinbefore disclosed. Various modifications and embodiments thereof can be made without departing from the spirit and scope thereof.

What is claimed is:

1. A non-invasive, quantitative somatosensory method for evaluating erectile dysfunction comprising:
   applying a variable temperature probe at an acclimation temperature to a glans penis of a male patient;
   starting at the acclimation temperature, raising the temperature of the variable temperature probe in 1° C. increments until the patient can correctly identify which temperature was warmer than the previous temperature at least two consecutive times, and noting such temperature as a first thermal threshold temperature;
   starting at the acclimation temperature, lowering the temperature of the variable temperature probe in 1° C. increments until the patient can correctly identify which temperature was cooler than the previous temperature at least two consecutive times, and noting such temperature as a second thermal threshold temperature; and
   applying a series of filaments to the glans penis of the male patient in ascending intensity until the patient can identify a sensation of light pressure and noting such intensity as a sensitivity threshold.

2. The method of claim 1 wherein the acclimation temperature is about 32° C.

3. The method of claim 2 wherein the variable temperature probe is applied to the dorsal midline of the glans penis.

4. The method of claim 1, wherein the step of applying the series of filaments to the glans penis of the male patient in ascending intensity, further comprises:
   applying a first filament perpendicular to the glans penis of the male patient for a first time period;
   applying a second filament perpendicular to the glans penis of the male patient for the first time period;
   applying a third filament perpendicular to the glans penis of the male patient for the first time period;
   applying a fourth filament perpendicular to the glans penis of the male patient for the first time period;
   applying a fifth filament perpendicular to the glans penis of the male patient for the first time period; and
   applying a sixth filament perpendicular to the glans penis of the male patient for the first time period.

5. The method of claim 4, wherein the first time period is about 1.5 seconds and
   the diameter of the first filament is substantially 2.83 mm, which corresponds to a target force of about 0.07 grams,
   the diameter of the second filament is substantially 3.61 mm, which corresponds to a target force of about 0.4 grams;
   the diameter of the third filament is substantially 4.31 mm, which corresponds to a target force of about 2.0 grams;
   the diameter of the fourth filament is substantially 4.56 mm, which corresponds to a target force of about 4.0 grams;
   the diameter of the fifth filament is substantially 5.07 mm, which corresponds to a target force of about 10 grams; and
   the diameter of the sixth filament is substantially to 6.65 mm which corresponds to a target force of about 300 grams respectively.

6. The method of claim 5 wherein the series of filaments are applied to the dorsal midline of the glans penis.

7. A non-invasive, quantitative somatosensory method for evaluating erectile dysfunction comprising:
   applying a variable temperature probe at an acclimation temperature to a glans penis of a male patient;
   starting at the acclimation temperature, raising the temperature of the variable temperature probe in 1° C. increments until the patient can correctly identify which temperature was warmer than a previous temperature at least two consecutive times and noting such temperature as a first thermal threshold temperature;
   starting at the acclimation temperature, lowering the temperature of the variable temperature probe in 1° C. increments until the patient can correctly identify which temperature was cooler than a previous temperature at least two consecutive times and noting such temperature as a second thermal threshold temperature; and applying a series of rods, each rod having a unique diameter to the glans penis of the male patient, in ascending diameter order for a time period until the patient can identify a smallest difference in circumference six consecutive times, and noting such difference as the spatial threshold.

8. The method of claim 7 wherein the acclimation temperature is about 32° C.

9. The method of claim 8 wherein the variable temperature probe is applied to the dorsal midline of the glans penis.

10. The method of claim 7, wherein the series of rods have circumferences in the range from about 12.5 mm to about 40 mm.

11. The method of claim 10, wherein each of the series of rods is applied for about 2 seconds.

12. The method of claim 11 wherein the series of rods are applied to the dorsal midline of the glans penis.

13. A non-invasive, quantitative somatosensory method for evaluating erectile dysfunction comprising:

applying a variable temperature probe at an acclimation temperature to a glans penis of a male patient;

starting at the acclimation temperature, raising the temperature of the variable temperature probe in 1° C. increments until the patient can correctly identify which temperature was warmer than a previous temperature at least two consecutive times and noting such temperature as a first thermal threshold temperature;

starting at the acclimation temperature, lowering the temperature of the variable temperature probe in 1° C. increments until the patient can correctly identify which temperature was cooler than the previous temperatures at least two consecutive times and noting such temperature as a second thermal threshold temperature;

applying a series of filaments to the glans penis of the male patient in ascending intensity until the patient can identify a sensation of light pressure and noting such intensity as a sensitivity threshold; and applying a series of rods, each rod having a unique diameter to the glans penis of the male patient, in ascending diameter order for a time period until the patient can identify a smallest difference in circumference six consecutive times, noting such difference as the spatial threshold.

14. The method of claim 13 wherein the acclimation temperature is about 32° C.

15. The method of claim 14 wherein the variable temperature probe is applied to the dorsal midline of the glans penis.

16. The method of claim 15, wherein the step of applying the series of filaments to the glans penis of the male patient in ascending intensity, further comprises:

applying a first filament perpendicular to the glans penis of the male patient for a first time period;

applying a second filament perpendicular to the glans penis of the male patient for the first time period;

applying a third filament perpendicular to the glans penis of the male patient for the first time period;

applying a fourth filament perpendicular to the glans penis of the male patient for the first time period;

applying a fifth filament perpendicular to the glans penis of the male patient for the first time period;

applying a sixth filament perpendicular to the glans penis of the male patient for the first time period.

17. The method of claim 16, wherein the first time period is 1.5 seconds and the diameter of the first filament is substantially 2.83 mm, which corresponds to a target force of 0.07 grams, the diameter of the second filament is substantially 3.61 mm, which corresponds to a target force of 0.4 grams;

the diameter of the third filament is substantially 4.31 mm, which corresponds to a target force of 2.0 grams;

the diameter of the fourth filament is substantially 4.56 mm, which corresponds to a target force of 4.0 grams;

the diameter of the fifth filament is substantially 5.07 mm, which corresponds to a target force of 10 grams, and the diameter of the sixth filament is substantially to 6.65 mm which corresponds to a target force of 300 grams respectively.

18. The method of claim 17 wherein the series of filaments are applied to the dorsal midline of the glans penis.

19. The method of claim 18, wherein the series of rods have circumferences in the range from about 12.5 mm to about 40 mm.

20. The method of claim 19, wherein each of the series of rods is applied for about 2 seconds.

21. The method of claim 20 wherein the series of rods are applied to the dorsal midline of the glans penis.

* * * * *